United States Patent [19]

Roberto et al.

[11] Patent Number: 5,023,256

[45] Date of Patent: Jun. 11, 1991

[54] PHARMACOLOGICALLY ACTIVE AMINOIMIDAZOPYRIDINES

[75] Inventors: Giani Roberto, Locate Triulzi; Parini Ettore, Cologno Monzese; Borsa Massimiliano, Vimodrone; Lavezzo Antonio, Lodi, all of Italy

[73] Assignee: Dompé Farmaceutici S.p.A., Milan, Italy

[21] Appl. No.: 519,982

[22] Filed: May 7, 1990

[30] Foreign Application Priority Data

May 8, 1989 [IT] Italy ............................... 20405 A/89

[51] Int. Cl.[5] ................ C07D 471/04; A61K 31/495; A61K 31/33
[52] U.S. Cl. .................... 514/253; 514/218; 514/254; 514/303; 540/575; 544/362; 546/118
[58] Field of Search ............ 546/118; 544/362; 540/575; 514/218, 253, 254, 303

[56] References Cited

U.S. PATENT DOCUMENTS 4,556,660 12/1985 Janssens et al. ..................... 546/118

FOREIGN PATENT DOCUMENTS 0282133 3/1988 European Pat. Off. .
0307014 7/1988 European Pat. Off. .
1260857 7/1968 United Kingdom ............... 546/118

OTHER PUBLICATIONS

Chemical Abstracts, vol. 67, p. 4110, 1967.

Primary Examiner—Mary C. Lee
Assistant Examiner—Lenora Miltenberger
Attorney, Agent, or Firm—Armstrong, Nikaido, Marmelstein, Kubovcik & Murray

[57] ABSTRACT

Novel imidazopyridine derivatives of formula:

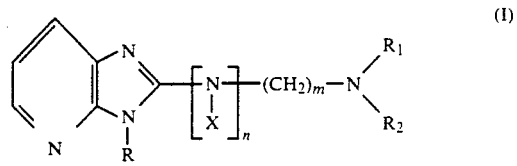

(I)

wherein,

R represents an alkoxyalky radical having 4–6 carbon atoms or a benzyl radical optionally substituted by a halogen atom, an alkyl or alkoxy radical having up to 3 carbon atoms, X represents hydrogen or an alkyl radical having up to 3 carbon atoms, n represents 0 or 1 m represents an integer of from 2 to 5 inclusive, $R_1$ and $R_2$ may be the same or different and represent a saturated or unsaturated alkyl radical containing up to 4 carbon atoms or they, taken together with the adjacent nitrogen atom, may form a pyrrolidine, piperazine or homopiperazine ring which may be optionally substituted by an alkyl radical containing up to 3 carbon atoms, provided that when n is zero also m is zero and —N($R_1$)$R_2$ represents the above defined piperazine or homopiperazine ring.

The compounds (I) have an antihistaminic activity.

7 Claims, No Drawings

PHARMACOLOGICALLY ACTIVE AMINOIMIDAZOPYRIDINES

The present invention relates to novel aminoimidazopyridine derivatives of the formula

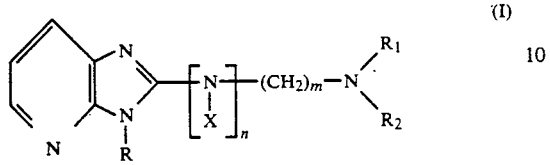

wherein,

R represents an alkoxyalkyl radical having 4–6 carbon atoms or a benzyl radical optionally substituted by a halogen atom, an alkyl or alkoxy radical having up to 3 carbon atoms, X represents hydrogen or an alkyl radical having up to 3 carbon atoms, n represents 0 or 1 m represents an integer of from 2 to 5 inclusive, $R_1$ and $R_2$ may be the same or different and represent a saturated or unsaturated alkyl radical containing up to 4 carbon atoms or, taken together with the adjacent nitrogen atom, they may form a pyrrolidine, piperazine or homopiperazine ring which may be optionally substituted by an alkyl radical containing up to 3 carbon atoms.

The invention also relates to compounds where n is zero, m is zero and $-N(R_1)R_2$ represents the above defined piperazine or homopiperazine ring and their non-toxic pharmaceutically acceptable acid addition salts with suitable organic and inorganic acid.

The alkoxyalkyl radical is preferably represented by 2-ethoxyethyl, 2-propoxyethyl, and propoxymethyl; among them it is preferred 2-ethoxyethyl radical.

The saturated alkyl radical is preferably represented by methyl, ethyl and propyl, while the unsaturated alkyl radical is preferably the allyl radical.

Among the non-toxic, pharmaceutically acceptable salts of compounds (I) are preferred the fumarate, maleate, succinate and hydrochloride: among them are particularly preferred the fumarate and hydrochloride.

The compounds of formula (I) are prepared reacting in the warm 2-chloro-3-nitropyridine with a suitable amine $H_2N-R$ wherein R has the above-mentioned meaning: the so formed nitropyridine (V) is then suitably reduced to aminopyridine (IV) which by treatment in the warm with urea is cyclized to imidazopyridine (III) and afterwards subjected to chlorination by means of phosphoryl chloride and gaseous hydrogen chloride to give 2-chloroimidazopyridine (II) which is reacted with the amino-derivative $[NH(X)]_n-(CH_2)_m-NR_1,R_2$ wherein X, n, m, $R_1$ and $R_2$ have the above cited meanings to give the compounds (I). The process may be schematically represented as following:

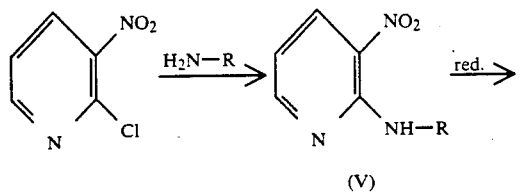

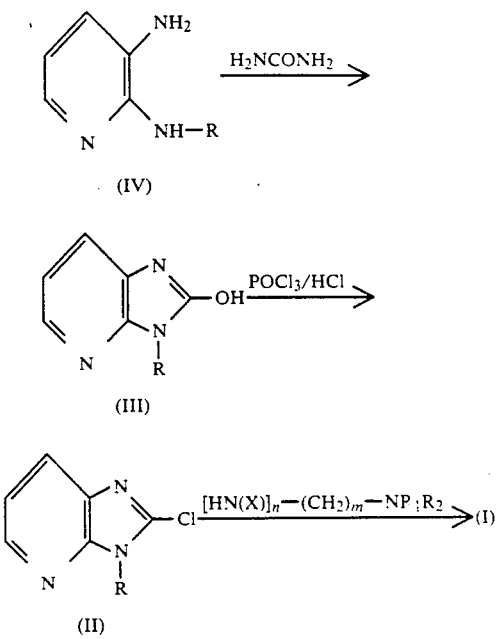

The compounds (I) have demonstrated to possess an interesting antihistaminic activity which has been evaluated studying either the effect on the mortality induced by histamine the effect on the sleeping time induced by sodium pento barbital and the acute toxicity ($LD_{50}$). The tests were carried out according to the following:

Effect on the Mortality Induced by Histamine

The method described by Romer D. et al. (Med. Welt, 17, 791, 1966) was followed and the tests were carried out on male albino guinea pigs (Dunkin-Hartley), weighing 350–450 g, which were kept in cages with a grid floor, on an empty stomach for 24 hrs with water ad libitum.

The compounds under examination were dissolved in 0.5% carboxy methylcellulose and orally administered to the animals 60 minutes before that the same animals were intravenously treated with 1,25 mg/kg of histamine dihydrochloride dissolved in saline solution. In the control animals, treated with carboxymethyl cellulose, the histamine dihydrochloride solution, intravenously administered, induced a 100% mortality.

It was evaluated $ED_{50}$ which corresponds to the amount of the compound able to inhibit 50% of the mortality induced by histamine: the estimation of $ED_{50}$ was carried out applying the 'probit' method (Finney D. J., Statistical methods in biological assay, pg 512, 1957).

Effect on the Sleeping Time Induced by Pentobarbital

The tests were carried out on male mice Swiss-Nos (Nossan, Correzzana, Milano) weighing 20–24 g, on an empty stomach for 18 hrs, according to the method described by R. Turner (Screening Methods in Pharmacology, Acad. Press, pg 70, 1965). The sleep was induced by intraperitoneal administration of 40 mg/kg sodium pentobarbital. The narcosis start was considered from the moment when the animal, lying on its back, lost its straightening reflex. The narcosis end was considered from the moment when the animal recovered such reflex.

The carrier or the compounds under examination were administered by intraperitoneal route at the dose 25 mg/kg, 30 minutes before the pentobarbital administration.

The resulting data are expressed as sleeping time increase percent in the treated animal group in comparison to the control animal group.

Evaluation of the Lethal Dose$_{50}$(LD$_{50}$)

The tests were carried out on Swiss Nos (Nossan; Correzzana, Milano) mice weighing 18–20 g each. The animals, divided into groups of 10 animals each (5M+5F), were on an empty stomach for 18 hrs, with water ad libitum, and kept in cages with a grid floor. The compounds (I) were dissolved in water or suspended in 0.5% carboxymethylcellulose and intraperitoneally administered to the animals (10 ml/kg). The number of mice which died within the following 6 hours was recorded. Upon the expiry of the sixth hour, the animals were allowed to eat up to the end of the experimentation which lasted 14 days. During this period all the toxic symptoms and the mortality occurring were noted.

The animals which died during the test period and those which were sacrificed at the end of the same, underwent autopsy for a macroscopic examination of their main organs. The experimental data were statistically compared with the $X^2$ method and LD$_{50}$ was extrapolated by the 'probit' method.

The data resulting from the tests carried out on some significant compounds of the class (I), evaluated in comparison to Terfenadine, a known H$_1$-antihistaminic of the commerce are given in the following Table.

TABLE

| Compound | Mortality induced by histamine ED$_{50}$p.o. μg/kg | Increase of sleeping time induced by pentobarbital 25 mg/kg % | Acute toxicity LD$_{50}$i.p. mg/kg |
| --- | --- | --- | --- |
| Example 1 | 33 | 183 | >100 |
| Example 2 | 0.007 | 76 | >100 |
| Terfenadine | 436 | 44 | 620 |

For therapeutic administration, the compounds according to the present invention are used in the form of pharmaceutical preparations which contain said compounds in admixture with pharmaceutically acceptable carriers such as an organic or inorganic solid or liquid excipient suitable for oral or parenteral administration. The compounds of the invention may be contained in these pharmaceutical preparations in the form of free base or in the form of their non-toxic acid addition salts.

The inorganic acids which may be employed to prepare these acid addition salts may be, for example, hydrochloric or sulphuric acid. The organic acids which may be employed are, for example, maleic, fumaric and succinic acid. The pharmaceutical preparations may be in solid form as capsules, tablets, dragees or in liquid form such as solutions, suspensions or emulsions. If desired, there may be included in the above preparations auxiliary substances such as stabilizing agents and other commonly used additives, or there may be contained other therapeutically active agents suitable to be administered together with the compounds of the invention. The dosage of the compounds will vary from the administration route and will also depend upon the age and condition of the patient.

The following Examples are given to better describe the invention without limiting it.

EXAMPLE 1

3-Benzyl-2-(4-methylpiperazin-1-yl)-3H-imidazo[4,5-b]pyridine fumarate

Grams 47.4 of 2-chloro-3-nitropyridine are refluxed for 2 hours in 600 ml toluene with 33 ml benzylamine and 31.8 g sodium carbonate. The reaction mixture is cooled to room temperature and 200 ml water are added thereto. The phases are separated, the organic phase evaporated to small volume, diluted with 400 ml isopropyl ether and kept under stirring for 30 minutes while cooling with water. It is filtered, washed with isopropyl ether, evaporated to dryness to give 46 g 2-benzylamino-3-nitropyridine melting at 81°–82° C.

A mixture consisting of 125 g Fe in powder, 160 ml 95% ethyl alcohol, 40 ml water and 2 ml 37% hydrochloric acid, are refluxed under stirring for 10 minutes; then it is cooled to about 70° C. and to the mixture 50 g 2-benzylamino-3-nitro-pyridine are added. It is heated under reflux for 1 hour, 6 g sodium bisulphite are added thereto, it is filtered in warm conditions and washed thoroughly with 95° C. boiling ethyl alcohol. The mixture is evaporated till dryness, the residue taken up with water and ethylacetate, the phases are separated and the organic phase evaporated till dryness. The residue is constituted by an oil which is taken up with 500 ml boiling cyclohexane and the insoluble removed therefrom. From the cyclohexane solution 16 g 2-benzylamino-3-aminopyridine, melting at 90°–91° C., crystallize.

Grams 10 2-benzylamino-3-amino pyridine and 3 g urea in 50 ml xylene are heated under reflux for 3 hours. The reaction mixture is then cooled to room temperature, the undissolved product filtered and washed with toluene; the solid dried in vacuo at 80° C. gives 5.1 g 3-benzyl-2-hydroxy-3H-imidazo[4,5-b]pyridine which, recrystallized from absolute ethyl alcohol, melts at 177°–179° C.

Grams 21 3-benzyl-2-hydroxy-3H-imidazo[4,5-b]pyridine in 330 ml phosphoryl chloride are refluxed until complete dissolution then gaseous hydrogen chloride is bubbled therein for 3 and a half hours. It is then cooled to room temperature and the undissolved product filtered and washed with toluene; the solution is evaporated in vacuo to a small volume and cautiously poured into ice. The solution is then filtered on charcoal and the filtrate adjusted to pH 7.5 by adding 30% ammonium hydroxyde. The undissolved product is separated by filtration, washed with water ed evaporated in vacuo to dryness, the product thus obtained suspended in 150 ml boiling toluene and the undissolved product filtered off. From the toluene solution are obtained by crystallization 5 g 3-benzyl-2-chloro-3H-imidazo[4,5-b]pyridine melting at 74°–76° C.

Grams 2.5 3-benzyl-2-chloro-3H-imidazo[4,5-b]pyridine and 4 ml N-methylpiperazine are heated at 130°–140° C. for 2 hours, then it is cooled, taken up with a few milliliters of chloroform, and separated by chromatography on silica gel column, first eluting with chloroform and then with chloroform:methyl alcohol (95:5). Therefore it is obtained 1 g 3-benzyl-2-(4-methylpiperazin-1-yl)-3H-imidazo[4,5-b]pyridine, which is dissolved in 5 ml absolute ethyl alcohol and added to a solution of 0.8 g fumaric acid in 15 ml absolute ethyl alcohol. It is kept under stirring overnight, the crystallized solid is separated and washed with absolute ethyl alcohol to obtain 0.8 g 3-benzyl-2-(4-methylpiperazin-1-yl)-3H-imidazo[4,5-b]pyridine fumarate melting at 165°–166° C.

EXAMPLE 2

3-Benzyl-2-(2-dimethylaminoethylamino)-3H-imidazo[4,5-b]pyridine dihydrochloride Grams 5 of 3-benzyl-2-chloro-3H-imidazo[4,5-b]pyridine and 9 ml N,N-dimethylethylenediamine are refluxed for 3 hours, then the amine in excess is removed by evaporation under vacum, the oily residue taken up with absolute ethyl alcohol and 10 ml 32% hydrochloric acid are added thereto, the solid crystalline filtered and washed with absolute ethyl alcohol. It is evaporated till dryness and 2.1 g 3-benzyl-2-(2-dimethylaminoethylamino)-3-H-imidazo[4,5-b]pyridine dihydrochloride melting at 262°–264° C. (with decomposition) are obtained.

EXAMPLE 3

3-(4-Fluorobenzyl)-2-(2-dimethylaminoethylamino)-3H-imidazo[4,5-b]pyridine

Operation is carried out similarly to what described in Example 2 using p-fluorobenzylamine to obtain 3-(4-fluorobenzyl)-2-(2-dimethylaminoethylamino)-3H-imidazo[4,5-b]pyridine

| Elementary analysis for $C_{17}H_{20}FN_5$ | | | |
|---|---|---|---|
| C | H | N | F |
| calculated % 65.16 | 6.43 | 22.35 | 6.06 |
| found % 65.34 | 6.41 | 22.17 | 6.00 |

EXAMPLE 4

3-(4-Fluorobenzyl)-2-(2-diethylaminoethylamino)-3H-imidazo[4,5-b]pyridine

Operation is carried out similarly to what described in Example 2 using first p-fluorobenzylamine and then, instead of N,N-dimethylethylenediamine, N,N-diethylethylenediamine to obtain 3-(4-fluorobenzyl)-2-(2-diethylaminoethylamino)-3H-imidazo[4,5-b]pyridine.

| Elementary analysis for $C_{19}H_{24}FN_5$ | | | |
|---|---|---|---|
| C | H | N | F |
| calculated % 66.84 | 7.09 | 20.51 | 5.56 |
| found % 66.71 | 7.01 | 20.32 | 5.68 |

EXAMPLE 5

3-(4-Fluorobenzyl)-2-(4-methylpiperazin-1-yl)-3H-imidazo[4,5-b]pyridine

Operation is carried out similarly to what described in Example 2 with the difference that it is first used p-fluoro-benzylamine and then N-methylpiperazine to give 3-(4-fluoro-benzyl)-2-(4-methylpiperazin-1-yl)-3H-imidazo[4,5-b]pyridine.

| Elementary analysis for $C_{18}H_{20}FN_5$ | | | |
|---|---|---|---|
| C | H | N | F |
| calculated % 66.44 | 6.20 | 21.52 | 5.84 |
| found % 66.30 | 6.19 | 21.50 | 5.87 |

EXAMPLE 6

3-Benzyl-2-[(N-methyl-N-(2-dimethylaminoethyl)amino]-3H-imidazo[4,5-b]pyridine dihydrochloride Operation is carried out similarly to what described in Example 2 with the difference that, instead of N,N-dimethylethylenediamine, it is used N'-methyl-N,N-dimethylethylenediamine to obtain 3-benzyl-2-[(N-methyl-N-(2-dimethylaminoethyl)amino]-3H-imidazo[4,5-b]pyridine which is isolated as dihydrochloride melting at 245°–248° C. (with decomposition).

EXAMPLE 7

3-Benzyl-2-(homopiperazin-1-yl)-3H-imidazo-[4,5-b]pyridine dihydrochloride

Operation is carried out similarly to what described in Example 1 with the difference that, instead of N-methylpiperazine, it is used homopiperazine to obtain 3-benzyl-2-(homopiperazin-1-yl)-3H-imidazo[4,5-b]pyridine which is isolated as dihydrochloride melting at 158°–160° C. (with decomposition).

EXAMPLE 8

3-Benzyl-2-(4-methylhomopiperazin-1-yl)-3H-imidazo[4,5-b]pyridine dihydrochloride Operation is carried out similarly to what previously described using N-methylhomopiperazine to obtain 3-benzyl-2-(4-methylhomopiperazin-1-yl)-3H-imidazo[4,5-b]pyridine which is isolated as dihydrochloride melting at 242°–243° C.

EXAMPLE 9

3-Benzyl-2-[(2-(4-methylpiperazin-1-yl)ethylamino]-3H-imidazo[4,5-b]pyridine

Operation is carried out similarly to what previously described using 2-(4-methylpiperazin-1-yl) ethylamine to obtain 3-benzyl-2-[2-(4-methylpiperazin-1-yl)ethylamino]-3H-imidazo[4,5-b]pyridine.

| Elementary analysis for $C_{20}H_{26}N_6$ | | |
|---|---|---|
| C | H | N |
| calculated % 68.54 | 7.48 | 23.98 |
| found % 68.39 | 7.53 | 24.05 |

EXAMPLE 10

3-(2-Etoxyethyl)-2-[(2-pyrrolidin-1-yl)ethylamino]-3H-imidazo[4,5-b]pyridine

Operation is carried out similarly to what previously described using first 2-ethoxyethylamine, and then 2-(pyrrolidin-1-yl)ethylamine to obtain 3-(2-ethoxyethyl)-2-[2-(pyrrolidin-1-yl)ethylamino]-3H-imidazo[4,5-b]pyridine.

| Elementary analysis for $C_{16}H_{25}N_5O$ | | |
|---|---|---|
| C | H | N |
| calculated % 63.34 | 8.31 | 23.08 |
| found % 63.42 | 8.27 | 23.14 |

EXAMPLE 11

3-(2-Ethoxyethyl)-2-(3-dimethylaminopropylamino)-3H-imidazo[4,5-b]pyridine

Operation is carried out as previously described using first 2-ethoxyethylamine, then 3-dimethylaminopropylamine to obtain 3-(2-ethoxyethyl)-2-(3-dimethylaminopropylamino)-3H-imidazo[4,5-b]pyridine.

| Elementary analysis for $C_{15}H_{25}N_5O$ | | | |
|---|---|---|---|
| | C | H | N |
| calculated % | 61.83 | 8.65 | 24.03 |
| found % | 62.00 | 8.75 | 23.98 |

EXAMPLE 12

3-(2-Ethoxyethyl)-2-[N-methyl-N-(2-dimethylaminoethyl)amino]-3H-imidazo[4,5-b]pyridine Operation is carried out as previously described using first 2-ethoxyethylamine, then N'-methyl-N,N-dimethylethylenediamine to obtain 3-(2-ethoxyethyl)-2-[N-methyl-N-(2-dimethylaminoethyl)amino]-3H-imidazo[4,5-b]pyridine.

| Elementary analysis for $C_{15}H_{25}N_5O$ | | | |
|---|---|---|---|
| | C | H | N |
| calculated % | 61.83 | 8.65 | 24.03 |
| found % | 62.04 | 8.71 | 23.94 |

EXAMPLE 13

3-(2-Ethoxyethyl)-2-(2-dimethylaminoethylamino)-3H-imidazo[4,5-b]pyridine

Operation is carried out as previously described using first 2-ethoxyethylamine and then N,N-dimethylethylenediamine to obtain 3-(2-ethoxyethyl)-2-(2-dimethylaminoethylamino)-3H-imidazo[4,5-b]pyridine.

| Elementary analysis for $C_{14}H_{23}N_5O$ | | | |
|---|---|---|---|
| | C | H | N |
| calculated % | 60.62 | 8.36 | 25.25 |
| found % | 60.93 | 8.24 | 25.21 |

EXAMPLE 14

3-(2-Ethoxyethyl)-2-(4-methylpiperazin-1-yl)-3H-imidazo[4,5-b]pyridine dihydrochloride Operation is carried out as previously described using first 2-ethoxyethylamine and then N-methylpiperazine to obtain 3-(2-ethoxyethyl)-2-(4-methylpiperazin-1-yl)-3H-imidazo[4,5-b]pyridine which is isolated as dihydrochloride melting at 172°–174° C. (with decomposition).

We claim:

1. An aminoimidazopyridine compound of the formula

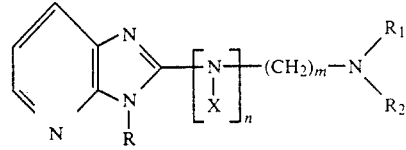

wherein
R represents an alkoxyalkyl radical containing 4–6 carbon atoms or a benzyl radical optionally substituted by a halogen atom, an alkyl or alkoxy radical having up to 3 carbon atoms;
X represents hydrogen or an alkyl radical having up to 3 carbon atoms;
n is 1;
m is an integer of from 2 to 5 inclusive; and
$R_1$ and $R_2$ are the same or different and represent a saturated or unsaturated alkyl radical containing up to 4 carbon atoms or they may form, together with the adjacent nitrogen atom, a pyrrolidine, piperazine or homopiperazine ring, optionally substituted with an alkyl radical containing up to 3 carbon atoms;
or a non-toxic, pharmaceutically acceptable acid addition salt thereof.

2. An aminoimidazopyridine compound according to claim 1, wherein R is a benzyl radical optionally substituted with a halogen atom or with an alkyl or alkoxy radical having up to 3 carbon atoms.

3. An aminoimidazopyridine compound according to claim 1, wherein R is 2-ethoxyethyl.

4. The aminoimidazopyridine compound according to claim 1, which is 3-benzyl-2-(2-dimethylaminoethylamino)-3H-imidazo[4,5-b]pyridine dihydrochloride.

5. An aminoimidazopyridine compound of the formula

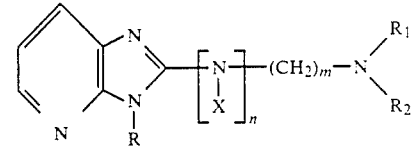

wherein
R represents an alkoxyalkyl radical containing 4–6 carbon atoms, or a benzyl radical optionally substituted by a halogen atom, an alkyl or alkoxy radical having up to 3 carbon atoms;
X represents hydrogen or an alkyl radical having up to 3 carbon atoms;
n is 0;
m is 0;
$R_1$ and $R_2$ form, together with the adjacent nitrogen atom, a piperazine or homopiperazine ring, optionally substituted with an alkyl radical containing up to 3 carbon atoms;
or a non-toxic, pharmaceutically acceptable acid addition salt thereof.

6. The aminoimidazopyridine compound according to claim 5 which is 3-benzyl-2-(4-methylpiperazin-1-yl)-3H-imidazo[4,5-b]pyridine fumarate.

7. A pharmaceutical composition comprising an antihistaminically effective amount of at least one compound according to any one of claims 2, 3, 4, 5 or 6 or a pharmaceutically acceptable salt thereof, in admixture with a pharmaceutically acceptable carrier.

* * * * *

UNITED STATES PATENT AND TRADEMARK OFFICE
CERTIFICATE OF CORRECTION

PATENT NO. : 5,023,256

DATED : June 11, 1991

INVENTOR(S) : Roberto GIANI et al

It is certified that error appears in the above-identified patent and that said Letters Patent is hereby corrected as shown below:

On the cover page, Item [75], the names of the inventors should read -- Roberto GIANI, Ettore PARINI, Massimiliano BORSA, Antonio LAVEZZO --.

Column 1, line 23, delete "O or".

Column 6, line 54, "Etoxyethyl" should read -- Ethoxyethyl --.

Signed and Sealed this

Seventh Day of April, 1992

Attest:

HARRY F. MANBECK, JR.

*Attesting Officer*     Commissioner of Patents and Trademarks